United States Patent

Gupta et al.

[11] Patent Number: 5,591,451
[45] Date of Patent: Jan. 7, 1997

[54] OIL-BASED TABLETING METHOD

[75] Inventors: Pramod K. Gupta, Gurnee; Francisco J. Alvarez, Lindenhurst; Susan J. Semla, Evanston, all of Ill.

[73] Assignee: Abbott Laboratories, Abbott Park, Ill.

[21] Appl. No.: 484,693

[22] Filed: Jun. 7, 1995

Related U.S. Application Data

[63] Continuation of Ser. No. 110,916, Aug. 24, 1993, abandoned.

[51] Int. Cl.$^6$ .................................................. A61K 9/20
[52] U.S. Cl. ............................................................ 424/464
[58] Field of Search ................................................ 424/464

[56] References Cited

U.S. PATENT DOCUMENTS 5,219,574  6/1993  Wehling et al. ........................ 424/464
5,225,201  7/1993  Beaurline .............................. 424/464

Primary Examiner—James J. Seidleck
Assistant Examiner—John M. Cooney, Jr.
Attorney, Agent, or Firm—Mona Anand; Thomas D. Brainard

[57] ABSTRACT

A pharmaceutical tablet containing a therapeutically active compound and between 5% and about 20% by weight of an oil, preferably selected from vegetable, mineral, animal and edible oils, as well as a method for preparing such tablets. Such tablets provide for the controlled release of the therapeutically active compound from the tablet and also enhance the stability of some therapeutically active compounds.

20 Claims, 9 Drawing Sheets

OIL-BASED TABLETING METHOD

This application is a continuation of U.S. patent application Ser. No. 08/110,916, filed on Aug. 24, 1993 which is now abandoned.

This invention relates to pharmaceutical tablets comprising an oil and a therapeutically active compound, as well as a method for preparing such tablets.

BACKGROUND OF THE INVENTION

The most commonly used route for systemically delivering therapeutically active compounds is the oral route. The most popular method of oral administration is by tablets. Generally, tablets are inexpensive and easy to make. For example, tablets can be made by tightly compressing an amount of a solid therapeutically active compound. However, most tablets contain other ingredients besides the therapeutically active compound. For example, a tablet may also include inactive fillers, binders, diluents, lubricants, disintegrants, coloring agents and flavoring agents.

A tablet is formulated so that any additional ingredients will not detrimentally interact with the therapeutically active compound and so that the therapeutically active compound is delivered systemically. For example, the hardness of the tablet can affect the dissolution rate of the tablet in vivo. While a tablet that is too hard will not easily dissolve, a tablet must be hard enough to withstand the forces of the manufacturing and the distribution processes.

In formulating a tablet, the patient is also considered and thus, often the tablet may contain a coloring agent, which makes the color of the tablet more pleasing to the patent. Similarly, a flavoring agent may be added to make the tablet more palatable.

Sometimes inert fillers are used to obtain the precise size and shape of the tablet desired. The filler is usually selected from a group of compounds that are inert with respect to the therapeutically active compound and that are suitable for consumption by the patient.

The most common method of making a tablet involves mixing the ingredients of the tablet and compressing the mixture in a mold to give it the desired shape and hardness. The mixture of ingredients is usually mechanically compressed by a machine. The compressed mixture may be either wet or dry. However, in a method where the mixture is wet, the mixture or tablet must be dried.

Lubricants can be added to the composition that is to be formed into a tablet to help reduce the frictional wear of the die and its associated parts. Binders may also be added to help promote the adhesion of the different ingredients of the mixture. Disintegrants help the tablet to disintegrate in vivo and thus help to deliver the therapeutically active compound contained in the tablet.

It is also sometimes desirable to coat the tablet. The coating may, for example, be a thin film of light-sensitive material to prevent decomposition of the tablet. Or, the film may have other purposes such as to mask a tablet's unpleasant taste or to delay the disintegration or dissolution of a tablet. A delay may be important, for some therapeutically active compounds irritate the stomach, and it may be desirable to delay the dissolution of the tablet containing such a compound until the tablet reaches the intestine.

Oils have been employed in tablets up to 5% by weight relative to the tablet. For example, vegetable oils have been used as lubricants in concentrations of 1% to 5% by weight relative to the tablet. It has also been noted that vegetable oils may prolong disintegration time of a tablet. *Introductory Medicinal Chemistry*, J. B. Taylor and P. D. Kennewell, Halsted Press—A Division of John Wiley & Sons, 1981, pp. 37–42. Some tablet compositions have included hydrogenated castor oils and/or hydrogenated cottonseed oils. However, both hydrogenated castor oil and hydrogenated cottonseed oil are solid at room temperature.

SUMMARY OF THE INVENTION

The present invention provides a pharmaceutical tablet for the systemic delivery of a therapeutically active compound comprising an effective amount of a therapeutically active compound and an oil in an amount of between 5% and about 20% by weight. This invention also provides a method for preparing a tablet for the systemic delivery of a therapeutically active compound comprising mixing a therapeutically active compound and an oil in an amount sufficient to provide between 5% and about 20% oil by weight and forming the mixture into a tablet. The present invention has the unexpected advantage that incorporation of between 5% and about 20% oil into a tablet provides for controlled release of the therapeutically active compound and may improve the stability of some therapeutically active compounds that have been incorporated into tablets.

BRIEF DESCRIPTION OF THE DRAWINGS

The present invention will be better understood in connection with the appended drawings, in which.

DETAILED DESCRIPTION OF THE INVENTION

The pharmaceutical tablet of the present invention contains an oil and a therapeutically active compound. The tablet may be used to systemically deliver a therapeutically active compound to a patient. As used herein, the phrase "therapeutically active compound" shall mean any compound for which systemic delivery is desired through oral administration. For example, a therapeutically active compound might be a drug or a vitamin. It is also within the scope of this invention to deliver more than one therapeutically active compound in a single tablet. Moreover, either hydrophobic or hydrophilic therapeutically active compounds may be used in the present invention.

The amount of therapeutically active compound that the tablet may contain will be controlled primarily by the desired systemic concentration of the therapeutically active compound. Generally, the larger the amount of the therapeutically active compound in a tablet, the higher the systemic concentration of the compound. Thus, the amount of therapeutically active compound should be optimized to give the systemic concentration that provides the desired therapeutic effect.

The tablet of the present invention also contains an oil. As used herein, the word "oil" shall include, but is not limited to, the classes of oils identified as vegetable, mineral, animal and edible. Generally, oils derived from animals or from plant seeds or nuts are chemically identical with fats, except that the oils are liquids at room temperature. These oils are composed primarily of triglycerides of the fatty acids. The mineral oils have two subclasses: petroleum and petroleum-derived. Petroleum is composed of a number of hydrocarbons, while the petroleum-derived oils include lubricants, engine oils and refined paraffin oils. Refined paraffin oils have been used in medicinal applications.

The vegetable oils include the oils derived chiefly from seeds or nuts and may include, for example, linseed, tung, otica, soybean, cottonseed, castor, coconut, corn, olive and palm oil. The animal oils include fish oils, fish liver oils, oleic acid and sperm oil. Citrus seed and peel oils may also be employed in this invention. The word "oil" shall also include oil-like substances such as vitamin E, which has been characterized as a pale yellow oil at room temperature.

The oils referred to above are illustrative of the oils which may be used in the present invention. These oils are not intended to be limiting, as any oil that is compatible with the biological organism for which the tablet is made may be used.

The amount of oil used in a tablet of the present invention may range from between 5% and about 20% by weight relative to the tablet. Preferably, the amount of oil is between 5% and about 15%, and more preferably between 5% and about 10%. Within these ranges, the amount of oil desired to be included in a tablet will depend on the desired characteristics of the tablet and the desired systemic delivery of the therapeutically active compound.

When oil is added to a tablet composition, the rate of release of the therapeutically active compound is decreased. Moreover, as the amount of oil is increased, the obtainable hardness is decreased. Therefore, it may be possible to obtain a maximal sustained delivery be varying the hardness and the oil content of a tablet. Maximization of sustained delivery may be achieved through simple trial and error.

The rate of dissolution of a tablet is related to the amount of therapeutically active compound that is released over time and delivered systemically. In general, the harder the tablet, the slower the rate of dissolution and the longer the time necessary for the therapeutically active compound to be delivered systemically.

A tablet may also, but need not, include other ingredients. For example, the tablet may include inactive fillers, binders, diluents, lubricants, disintegrants, coloring agents and flavoring agents. Some of the commonly used diluents include, but are not limited to, spray dried dextrose, lactose, calcium triphosphate, sodium chloride and microcrystalline cellulose. Some commonly used binders include, but are not limited to, acacia, ethyl cellulose, gelatin, glucose syrups, starch mucilage, polyvinyl pyrrolidone, sodium alginate and sucrose syrups. Some commonly used lubricants include, but are not limited to, magnesium stearate, stearic acid, talc, vegetable oils, colloidal silica and polyethylene glycol. Some commonly used disintegrants include, but are not limited to, starch, alginic acid, microcrystalline cellulose, crospovidone and sodium lauryl sulfate. Some commonly used inert fillers include, but are not limited to, silica, Avicel™ (microcrystalline cellulose), lactose, starch and mannitol. Avicel™ may be obtained from the FMC Corporation, Illinois, in two grades, Avicel™ PH 101 (mean particles size of 50 mm) and Avicel™ PH 102 (mean particle size of 100 mm). Either of the two grades of Avicel™ may be used in the present invention.

In addition, the tablets may also include sustained release agents such as, but not limited to, sodium alginate, Compritol™ 888 ATO (glyceryl behenate, from Gattefosse, N.J. polyethylene glycol (PEG), and hydroxypropyl methylcellulose (HMPC). Sustained release agents are also sometimes referred to as controlled release agents. It is also recognized that any other ingredient that is used in the art in tablet compositions and that does not interact detrimentally with the therapeutically active compound to be delivered systemically may also be incorporated into a tablet.

The present invention also provides a method for the preparation of a tablet for the systemic delivery of a therapeutically active compound. The method comprises mixing at least one therapeutically active compound with between 5% and about 20% by weight of an oil and forming the mixture into a tablet. The mixture may also include any of above-mentioned ingredients or any other compound or compositions that are known in the art to be included in tablets.

The formation of a tablet may be by any method that is known in the art for forming tablets. The most common method is the compression method. In the compression method, the components of a tablet are mixed, either wet or dry, and then an amount of the composition is applied to a mold. A die then compresses the mixture in the mold, forming a tablet. If the process is a wet process, the composition or tablet must be dried. A tablet can also be coated as described above by those methods known in the art for coating tablets.

While not wishing to be bound to theory, it is thought that the stability of certain compounds may be enhanced by the use of oils in tablet compositions. The use of an oil can reduce the moisture uptake of a tablet. Because the moisture uptake of a tablet is reduced, hydrolysis, oxidation and other mechanisms by which degradation of therapeutically active compounds can occur may be attenuated, and the storage life of certain therapeutically active compounds in tablet form may be extended. Moreover, the strict moisture-free conditions tinder which some tablets containing such sensitive compounds are manufactured may be relaxed.

It is anticipated that the tablets of the present invention may be suited not only for oral but also for rectal or vaginal use. When used in such a fashion, the tablets are expected to have the advantages of greater ease of handling when compared to conventional suppositories, and of improved physico-mechanical characteristics and comfort when compared to other rectal or vaginal tablets. It is further anticipated that the tablets of the invention may be used in veterinary medicine as well as human medicine.

The following examples further illustrate the invention and are not to be construed as limiting of the specification and the claims in any way. In the examples, all percentages of tablet ingredients are given as percentages by weight relative to the total tablet weight, and the light mineral oil in each case was obtained from Witco Company of Houston, Tex.

EXAMPLE 1

Figure 1:
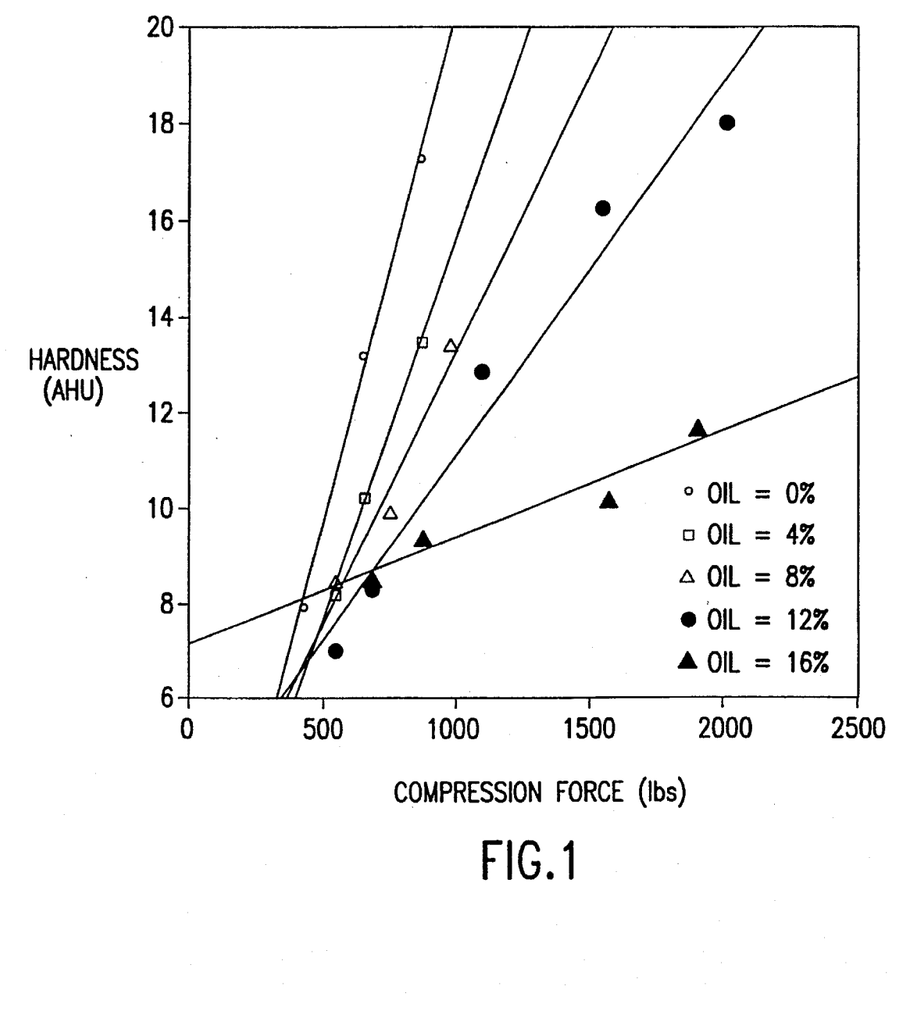
FIG. 1 is a plot that shows the relationship between the hardness of tablets containing an oil and the compression force used to make the tablets.

Hardness of Tablets Containing an Oil 250 mg tablets were prepared containing 0, 4, 8, 12 or 16% light mineral oil, 7.5% silica and an amount of Avicel™ microcrystalline cellulose to make 250 mg. The tablets were made by compressing 250 mg of the mixture at various compression forces. The hardness of the tablets was then measured, and FIG. 1 shows the results. (The unit for hardness used in herein is the Abbott Hardness Units (AHU), which was developed and is used by Abbott Laboratories. Many of the tablets commercially sold by Abbott Laboratories have hardnesses rated in AHU. The commercially sold tablets may be used for comparison when using other systems which measure hardness.) Generally, it is desired for a tablet to have a hardness above 6 AHU, as were all of the hardness measured.

EXAMPLE 2

Figure 2:
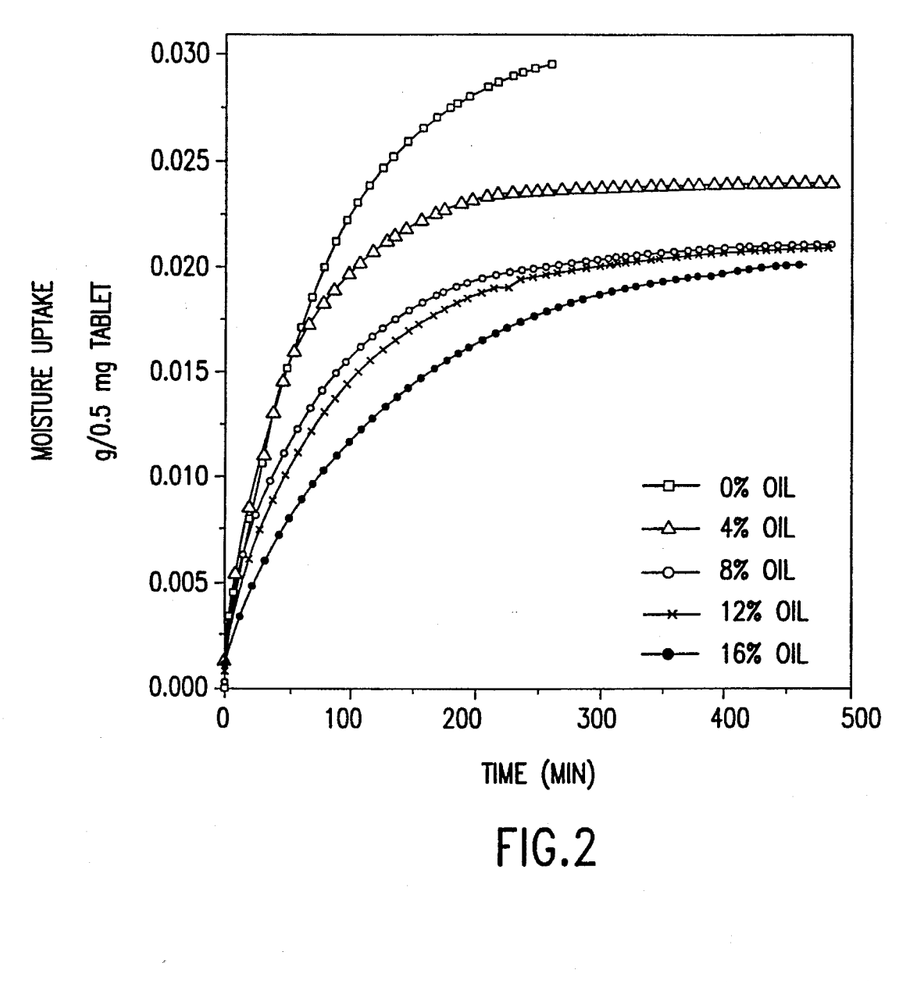
FIG. 2 is a plot that shows the relationship between moisture uptake for tablets containing an oil and time.

Moisture Uptake of Tablets Containing an Oil 250 mg tablets having a hardness of 8 AHU were prepared containing 0, 4, 8, 12 or 16% light mineral oil, 7.5% silica and an amount of Avicel™ microcrystalline cellulose to make 250 mg. Two tablets having the same composition were then placed on a moisture uptake device, a device which contains a balance and measures the weight increase over time. The weight increase was assumed to be due to moisture uptake of the tablet. The relative humidity of the atmosphere surrounding the tablets was kept at a constant 75% and the temperature was maintained at 25° C. The results, shown in FIG. 2, demonstrate the reduced mosture uptake resulting from the inclusion of oil at increased concentrations.

EXAMPLE 3

Release in a Water Solution of Tiagabine-HCl from Tablets Containing an Oil

Figure 3:
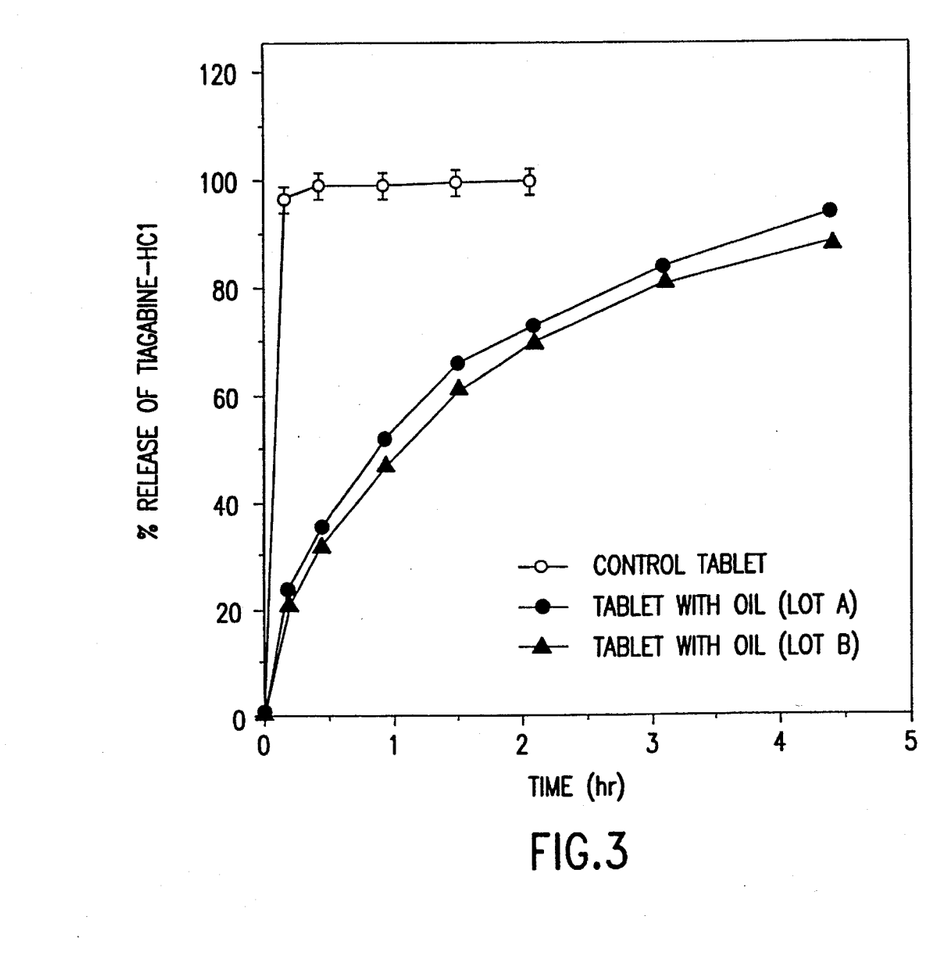
FIG. 3 is a plot that shows the relationship between the amount of tiagabine-HCl released in water by tablets containing an oil and time.

Two lots, A and B, of 250 mg tablets were prepared containing 10% light mineral oil, 6.4% tiagabine-HCl [((R)-N-(4,4-di(3-methyl-2-thienyl(-but-3-enyl)-nipectotic acid, from NOVO Industri A/S, France)], 1% vitamin E, 7.5.1% Avicel™ microcrystalline cellulose. As a control, tablets containing 4.2% tiagabine-HCl 35% mannitol, 58.2% Avicel™ microcrystalline cellulose, 1% citric acid, 0.25% BHA (butylated hydroxy anisole), 0.25% BHT (butylated hydroxy toluene), 1% magnesium stearate, 0.5% Sterotex K™ hydrogenated cottonseed oil (Karlshamnf, Columbus, Ohio) and 0.5% stearic acid were used. Each tablet was then placed in water at 37° C. The water was stirred with a paddle at 50 rpm and samples of the water were taken at various times and analyzed for tiagabine-HCl content. FIG. 3 shows the results of the mean of two independent experiments with each tablet composition, and demonstrates the delayed release of drug obtained by inclusion of oil into the tablet.

EXAMPLE 4

Figure 4:
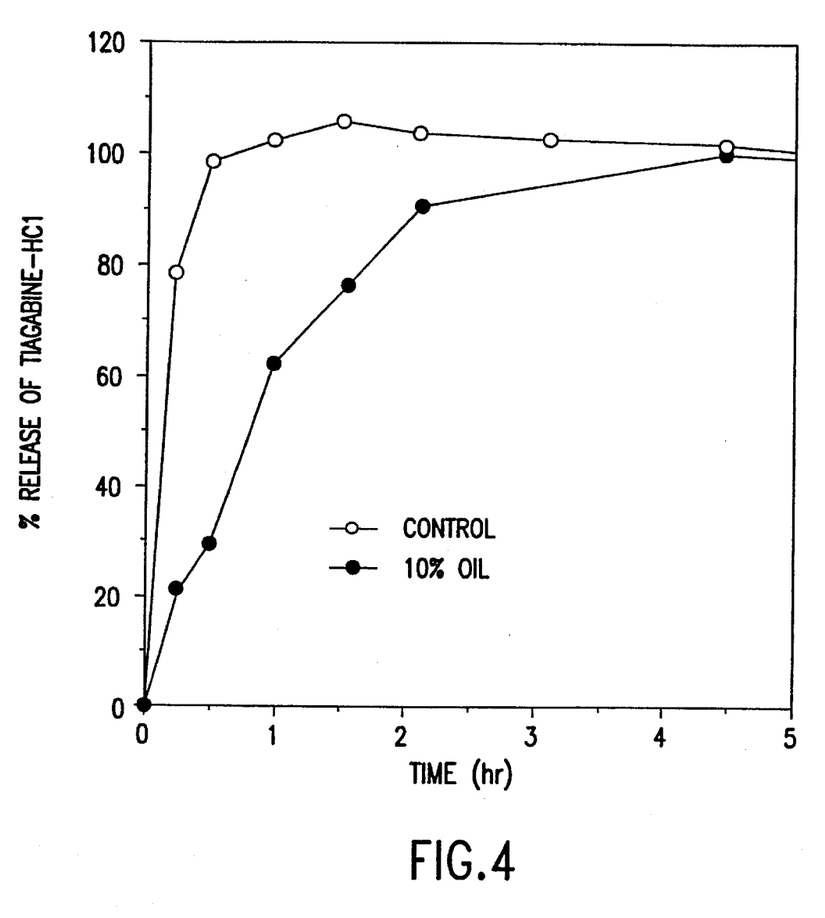
FIG. 4 is a plot that shows the relationship between the amount of tiagabine-HCl released in simulated gastric fluid by tablets containing an oil and time.

Release in Simulated Gastric Fluid of Tiagabine-HCl from Tablets Containing an Oil 250 mg tablets were prepared containing 10% light mineral oil, 3.2% tiagabine-HCl, 1% vitamin E, 7.5% silica and an amount of Avicel™ microcrystalline cellulose to make. 250 rag. As a control, tablets containing 3.2% tiagabine-HCl 1% vitamin E, 7.5% silica and an amount of Avicel™ microcrystalline cellulose to make 250 mg were made. The tablets were then placed in a simulated gastric fluid solution at 37° C. For this example and all examples herein which used simulated gastric fluid, the simulated gastric fluid was prepared by combining 2g of sodium chloride, 3.2g of pepsin, and 7 ml hydrochloric acid in a 1000 ml of water. The pH of the resultant solution was about 1.2 The simulated gastric fluid solution containing a tablet was stirred with a paddle at 50 rpm and samples of the solution were taken at various times and analyzed for tiagabine-HCl content. FIG. 4 shows the results, which demonstrate the delayed release of drug obtained by inclusion of oil into the tablet. (The data plotted in FIG. 4 are the result of the mean of two independent experiments with each tablet composition.)

EXAMPLE 5

Release in Simulated Gastric Fluid of Tiagabine-HCl from Tablets Containing an Oil and a

Sustained Release Compound 250 mg tablets containing each of the following were prepared:

1. 3.2% tiagabine-HCL, 10% light mineral oil, 1% vitamin E, 7.5% silica and an amount of Avicel™ to make 250 mg.
2. 3.2% tiagabine-HCL, 10% light mineral oil, 1% vitamin E, 7.5% silica, 15% sodium alginate and an amount of Avicel™ to make 250 mg.
3. 3.2% tiagabine-HCL, 10% light mineral oil, 1% vitamin E, 7.5% silica, 15% hydroxypropyl methylcellulose (HPMC) and an amount of Avicel™ microcrystalline cellulose to make 250 mg.

Figure 5:
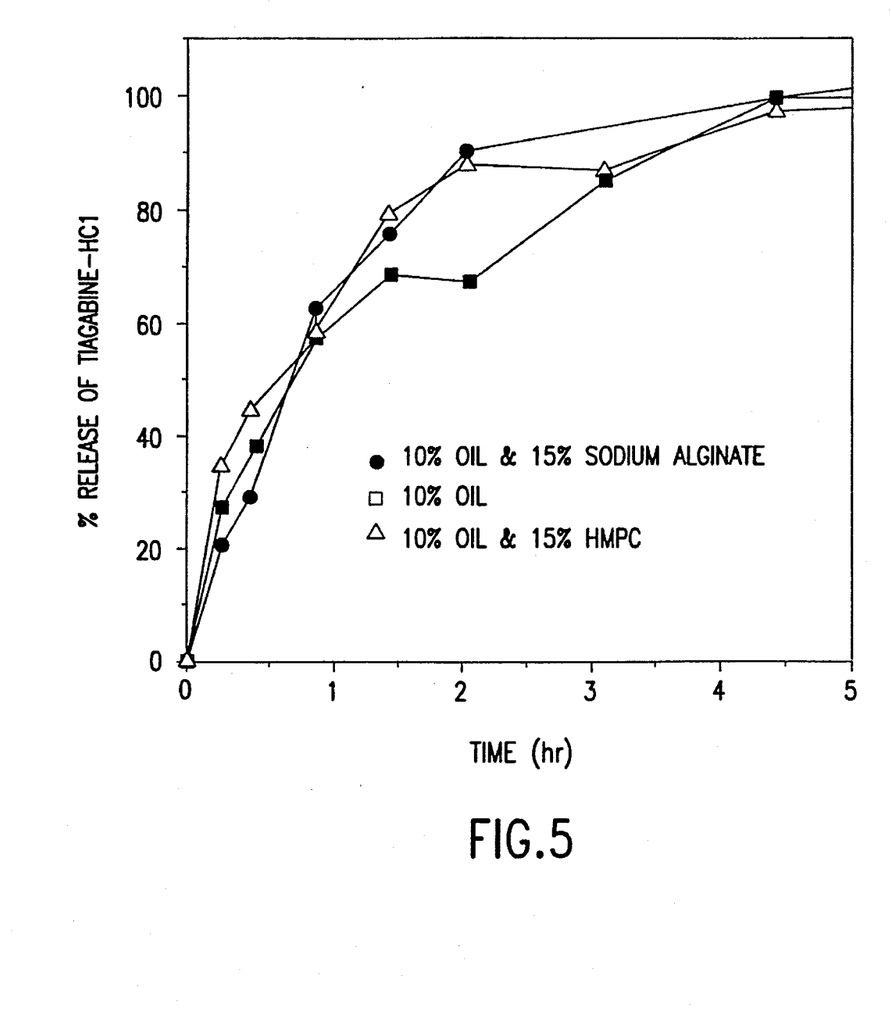
FIG. 5 is a plot that shows the relationship between the amount of tiagabine-HCl released in simulated gastric fluid by tablets containing an oil and time.

Each tablet was placed in a simulated gastric fluid solution that was stirred by a paddle at 50 rpm and maintained at 37° C. Samples of the fluid were taken at various times and the amount of tiagabine-HCl released determined by analysis of the samples. FIG. 5 shows the results. (The data used for FIG. 5 represent the mean of two repetitions for each tablet composition.)

EXAMPLE 6

Figure 6:
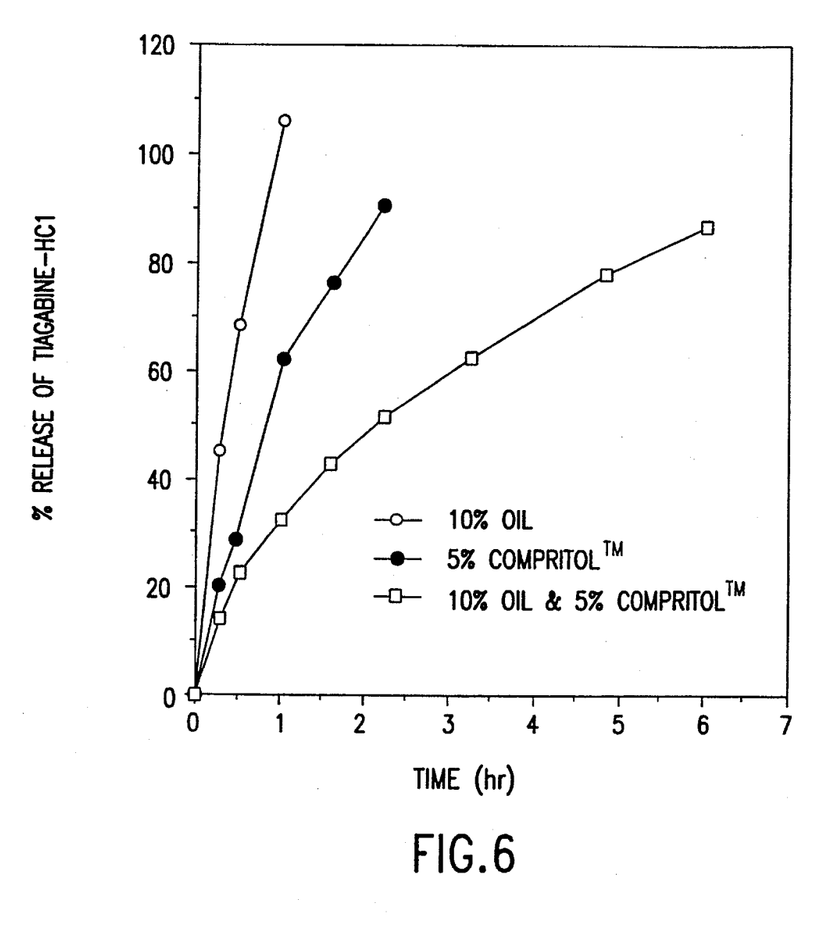
FIG. 6 is a plot that shows the relationship between the amount of tiagabine-HCl released in simulated gastric fluid by tablets containing an oil and time.

Release in Simulated Gastric Fluid of Tiagabine-HCl from Tablet Containing an Oil and Glyceryl Behenate 250 mg tablets containing 3.2% tiagabine-HCl, 0% or 10% light mineral oil and 0% or 5% glyceryl behenate (Gattefosse), a compound which provides sustained release, 1% vitamin E, 7.5% silica, and an amount of Avicel™ microcrystalline cellulose to bring the weight of the composition to 250 mg, were prepared to a hardness of 10–12 AHU. Each tablet was placed in a solution of simulated gastric fluid which was maintained at 37° C. and stirred at 50 rpm. Samples of the fluid were taken over time and analyzed for tiagabine-HCl content. The results are shown in FIG. 6. (The data for FIG. 6 were obtained by taking the mean of two repetitions for each tablet composition.)

EXAMPLE 7

Figure 7:
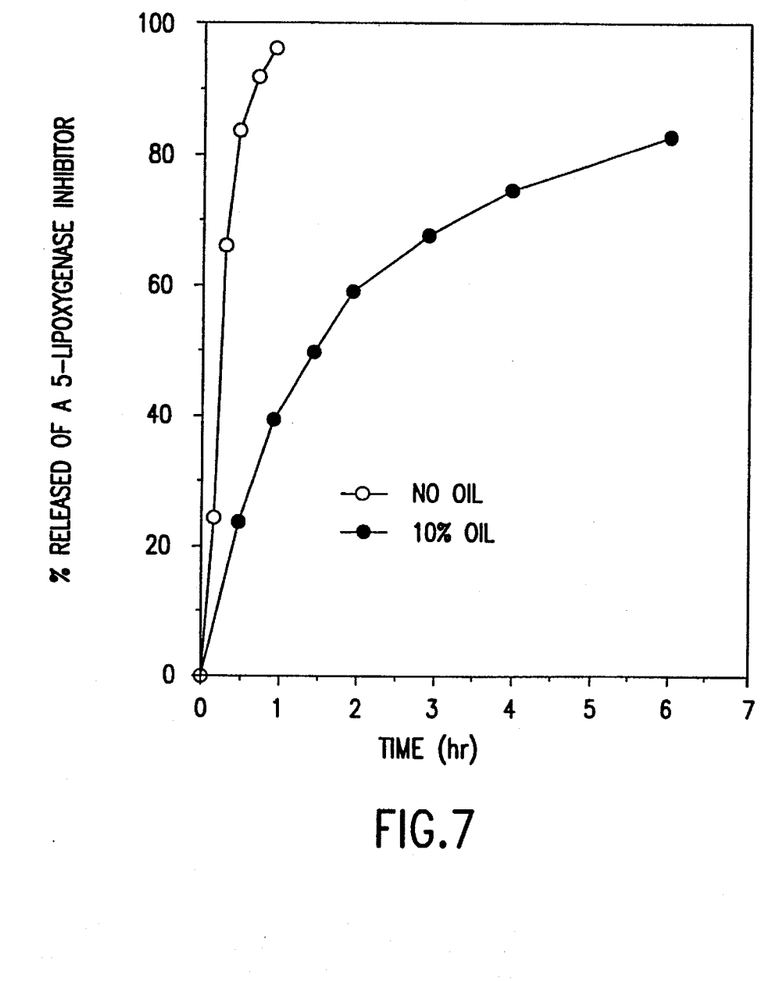
FIG. 7 is a plot that shows the relationship between the amount of a 5-lipoxygenase inhibitor released in a sodium dodecyl sulfate solution by tablets containing an oil and time.

Release of 5-Lipoxygenase Inhibitor from Tablets Containing an Oil 250 mg tablets containing 10% of a first 5-lipoxygenase inhibitor [N-( 1-(benzo[b]-thienyl-2-yl)ethyl)-N-hydroxyurea, from Abbott Laboratories], 10% light mineral oil, 7.5% silica and 72.5% Avicel™ microcrystalline cellulose were prepared at a hardness of 14 AHU. Tablets containing 50% 5-lipoxygenase inhibitor, 20% starch, 10% Avicel™ microcrystalline cellulose, 6% sodium starch glycolate, 5% Klucel™ hydroxypropyl cellulose (from Hercules, N.Y.), 5% Crospovidone™ (an insoluble form of polyvinylpyrrolidone, or PVP, from BASF), 3% talc and 1% magnesium stearate were used a controls. The tablets were placed in a 25–50 mM solution of sodium dodecyl sulfate maintained at 37° C. and stirred at 50 rpm. Samples of the solution were taken over time and the samples were analyzed for 5-lipoxygenase inhibitor content. FIG. 7 shows the results, which demonstrate the delayed release of drug obtained by inclusion of oil into the tablet.

EXAMPLE 8

Figure 8:
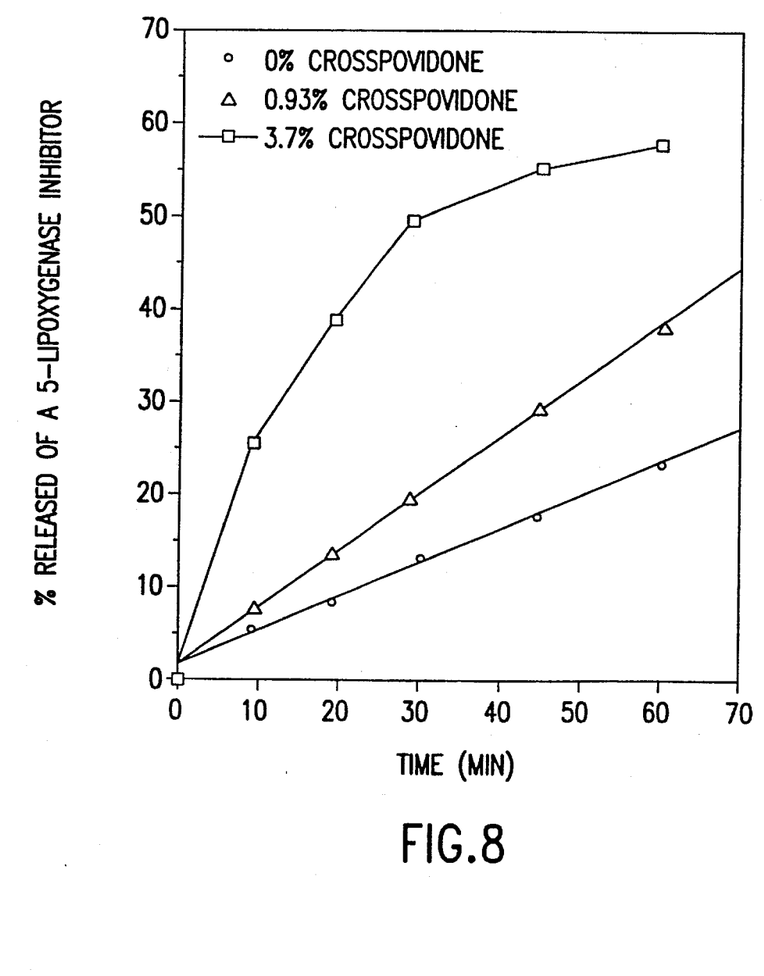
FIG. 8 is a plot that shows the relationship between the amount of a 5-lipoxygenase inhibitor released in a phosphate buffer solution by tablets containing an oil and time.

Release of a 5-Lipoxygenase Inhibitor From Tablets Containing an Oil and a Superdisintegrant 280 mg tablets were prepared containing 25 mg of the 5-lipoxygenase inhibitor of Example 7, 17.7% olive oil, 10.7% silica, and 0, 0.93 or 3.7% Crospovidone™ PVP as superdisintegrant, and an amount of Avicel™ microcrystalline cellulose sufficient to bring the composition to 280 mg. All tablets were maintained at a hardness of 8 AHU. Each tablet was placed in a 0.05M phosphate buffer solution that was kept at 37° C. and was stirred at 50 rpm. Samples of the solution were taken over time and analyzed for 5-lipoxygenase inhibitor content. FIG. 8 shows the results, which demonstrate the increased rate of release of drug obtained by inclusion of an superdisintegrant into the tablet.

EXAMPLE 9

Figure 9:
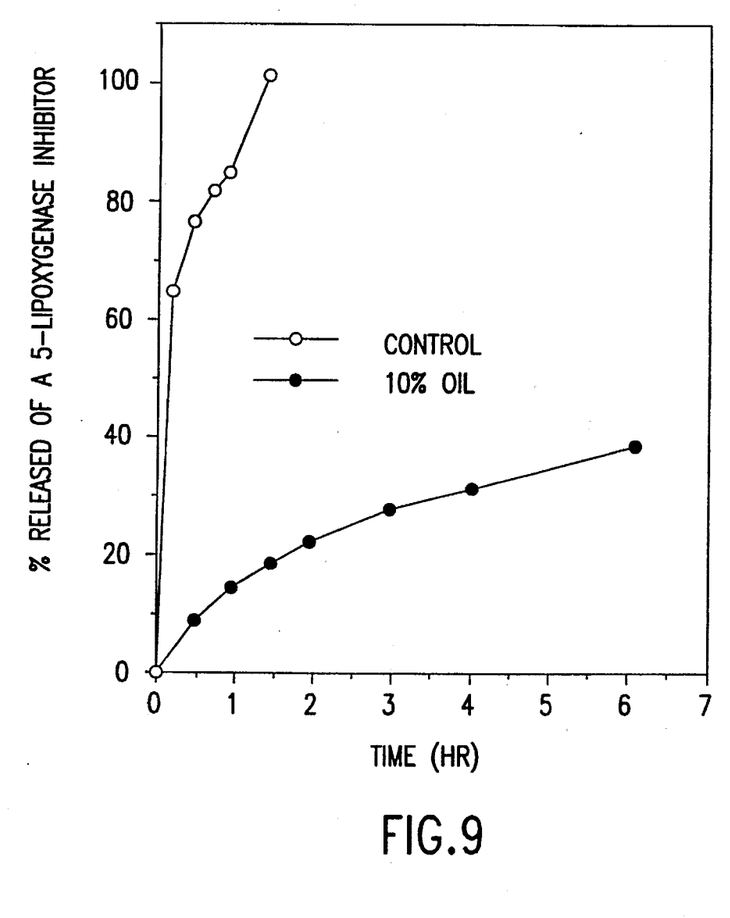
FIG. 9 is a plot that shows the relationship between the amount of another 5-lipoxygenase inhibitor released in a sodium dodecyl sulfate solution by tablets containing an oil and time.

Release of a 5-Lipoxygenase Inhibitor From Tablets Containing an Oil 250 mg tablets containing 10% of a second 5-lipoxygenase inhibitor [R-(+)-N-[3-[5-(4-fluorophenoxy)-2-furanyl]-1-methyl-2-propynyl]-N-hydroxyurea, from Abbott Laboratories], 10% light mineral oil, 7.5% silica and 72.5% Avicel™ microcrystalline cellulose were prepared. All tablets were maintained at a hardness of 13 AHU. A tablet containing 10% 5-lipoxygenase inhibitor, 10% starch, 65% Avicel™ microcrystalline cellulose, 5% Crosscarmelose™ hydroxypropyl cellulose binder (from Hercules, N.Y.), 4% talc, 5% Klucel™ hydroxypropyl cellulose and 1% magnesium stearate was used as a control. Each tablet was placed in a 25 mM sodium dodecyl sulfate solution maintained at 37° C. and stirred at 50 rpm. Samples of the solution were taken over time and analyzed for 5-lipoxygenase inhibitor content. FIG. 9 shows the results, which demonstrate the delayed release of drug obtained by inclusion of oil into the tablet.

EXAMPLE 10

Disintegration Time of Tablets Containing an Oil and Other Ingredients

Tablets were made and maintained at hardnesses between 11 and 16 AHU. Each tablet contained 3.2% tiagabine-HCl, 10% light mineral oil, 1% vitamin E, 7.5% silica, an additional ingredient as shown in Table 1 and enough Avicel™ microcrystalline cellulose filler to bring the total weight of the composition to 250 mg. Control tablets containing 3.2% tiagabine-HCl, 1% vitamin E, 7.5% silica and an ingredient as shown in Table 1 and enough Avicel™ microcrystalline cellulose filler to bring the total weight of the composition to 250 mg were also prepared. Each tablet was placed in a USP Tablet Disintegration Tester in a solution of simulated gastric fluid that was maintained at 37° C. The disintegration time of the tablets was measured. Table 1 below shows the results.

TABLE 1

Effect on Tablet Disintegration Rate of Various Excipients

| Ingredient | Tablet Hardness (AHU) | Disintegration Time (Minutes) Oil-Free Tablets | Disintegration Time (Minutes) Oil-Based Tablets |
|---|---|---|---|
| None | 12 | 3.3 | 34.2 |
| 15% Sodium Alginate | 11 | >360 | >360 |
| 10% HPMC (E4M) | 13 | 5.1 | 107.4 |
| 15% HPMC (E4M) | 13 | 1.5 | 244.8 |
| 20% HPMC (E4M) | 11 | 85.8 | 360 |
| 5% Compritol ™ | 12 | 9.0 | 105 |
| 10% Compritol ™ | 10 | 19.8 | 190.8 |
| 5% PEG (m.w. 200,000) | 14 | 1.2 | 6.6 |
| 5% HPMC (K15M) | 15 | 0.6 | 3.0 |
| 15% HPMC (K15M) | 13 | >300 | >300 |
| 5% HPMC (K100M) | 16 | 0.6 | 5.7 |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the active compounds, oils, other excipients and/or methods of the invention, may be made without departing from the spirit and scope thereof.

We claim:

1. A pharmaceutical tablet for the systemic, sustained-release delivery of a therapeutically active compound prepared by a process comprising the steps of:

(a) dispersing the therapeutically active compound in an oil, (b) mixing the compound/oil dispersion with a carrier silica; and (c) forming the dispersion/carrier mixture into a tablet;

wherein the oil is present in an amount of between 5% and about 20% by weight and provides a prolonged or sustained release of compound from the tablet.

2. A tablet according to claim 1 wherein the amount of oil is between 5% and 15% by weight.

3. A tablet according to claim 1 wherein the amount of oil is about 10% by weight.

4. A tablet according to claim 1 wherein the oil is selected from the group consisting of vegetable, mineral, animal and edible oils.

5. A tablet according to claim 1 wherein the oil is a vegetable oil selected from the group consisting of linseed, tung, otica, soybean, cottonseed, castor, coconut, corn, olive and palm oil.

6. A tablet according to claim 1 wherein the oil is an animal oil selected from the group consisting of fish oils, fish liver oils, oleic acid and sperm oil.

7. A tablet according to claim 1 wherein the oil is a mineral oil selected from the group consisting of petroleum and refined paraffin oils.

8. A tablet according to claim 7 wherein the mineral oil is light mineral oil.

9. A tablet according to claim 1 wherein the oil is selected from the group consisting of citrus peel oils and citrus seed oils.

10. A method for preparing a pharmaceutical tablet for the systemic, sustained-release delivery of a therapeutically active compound comprising the steps of:

(a) dispersing the therapeutically active compound in an oil, (b) mixing the compound/oil dispersion with a carrier silica; and (c) forming the dispersion/carrier mixture into a tablet;

wherein the oil is present in an amount of between 5% and about 20% by weight and provides a prolonged or sustained release of compound from the tablet.

11. A method according to claim 10 wherein the amount of oil is between 5% and 15% by weight.

12. A tablet according to claim 10 wherein the amount of oil is about 10% by weight.

13. A method according to claim 10 wherein the oil is selected from the group consisting of vegetable, mineral, animal and edible oils.

14. A method according to claim 10 wherein the oil is a vegetable oil selected from the group consisting of linseed, tung, otica, soybean, cottonseed, castor, coconut, corn, olive and palm oil.

15. A method according to claim 10 wherein the oil is an animal oil selected from the group consisting of the fish oils, fish liver oils, oleic acid and sperm oil.

16. A method according to claim 10 wherein the oil is a mineral oil selected from the group consisting of petroleum and refined paraffin oils.

17. A method according to claim 16 wherein the mineral oil is light mineral oil.

18. A method according to claim 10 wherein the oil is selected from the group consisting of citrus peel oils and citrus seed oils.

19. A method according to claim 10 wherein the fixture that is formed into a tablet is wet.

20. A method according to claim 10 comprising the additional step of coating the tablet formed in step (c).

* * * * *

UNITED STATES PATENT AND TRADEMARK OFFICE
CERTIFICATE OF CORRECTION

PATENT NO.   : 5,591,451
DATED        : January 7, 1997
INVENTOR(S)  : Gupta, et. Al.

It is certified that error appears in the above-indentified patent and that said Letters Patent is hereby corrected as shown below:

Column 10, line 24, change "fixture" to --mixture--.

Signed and Sealed this

Twentieth Day of May, 1997

Attest:

BRUCE LEHMAN

Attesting Officer

Commissioner of Patents and Trademarks